United States Patent [19]
Balfour et al.

[11] Patent Number: 5,110,292
[45] Date of Patent: May 5, 1992

[54] ENDOSSEOUS IMPLANT SYSTEM WITH INTERNAL JAM NUT

[75] Inventors: Alan R. Balfour, Oceanside; Donald E. Hendricks, San Diego, both of Calif.

[73] Assignee: Calcitek, Inc., Carlsbad, Calif.

[21] Appl. No.: 641,887

[22] Filed: Jan. 16, 1991

Related U.S. Application Data

[63] Continuation-in-part of Ser. No. 575,315, Aug. 30, 1990, abandoned.

[51] Int. Cl.⁵ .................................................. A61C 8/00
[52] U.S. Cl. .................................................. 433/173
[58] Field of Search ............... 433/173, 174, 175, 220, 433/221, 176

[56] References Cited

U.S. PATENT DOCUMENTS

| | | | |
|---|---|---|---|
| 2,745,180 | 5/1956 | Kiernan | 32/10 |
| 3,708,883 | 1/1973 | Flander | 32/10 A |
| 4,968,250 | 11/1990 | Small | 433/173 |

FOREIGN PATENT DOCUMENTS

| | | | |
|---|---|---|---|
| 0313222 | 4/1989 | European Pat. Off. | 433/174 |
| 0317688 | 5/1989 | European Pat. Off. | 433/173 |
| 0770696 | 3/1957 | United Kingdom | 433/174 |

Primary Examiner—Gene Mancene
Assistant Examiner—Nicholas D. Lucchesi
Attorney, Agent, or Firm—John R. Merkling

[57] ABSTRACT

An endosseous dental implant system comprising an artificial root and a coronal portion. Interposed between the artificial root and the coronal portion is an adjustable internal jam nut for providing a selected preload when the coronal portion is mounted in the artificial root.

5 Claims, 1 Drawing Sheet

ENDOSSEOUS IMPLANT SYSTEM WITH INTERNAL JAM NUT

This is a continuation-in-part of copending application Ser. No. 07/575,315 filed on Aug. 30, 1990, now abandoned.

FIELD OF THE INVENTION

This invention relates to endosseous implants and, particularly, to dental implants.

BACKGROUND OF THE INVENTION

Successful endosseous implants date from about 1968, at which time a biocompatible metal blade was fitted into a prepared elongate receptor site. The blade itself was perforated or vented to allow bone and blood vessels to reunite readily. A projected metal head, either unitary with or detachable from the blade, provided an anchor for attachment of a fixed bridge. Another endosseous metal implant design is the basket type having a projecting metal head. This implant is used specifically for partial support of a fixed bridge. Neither the blade nor the basket implant is designed or adapted for use as an anchor for overdentures or for use as a freestanding single tooth replacement to support a single crown.

There are at present a number of different dental implant systems in use. Most systems include an artificial root or implant cylinder which is placed into a custom bored hole in the jaw bone. A prosthetic coronal portion is attached to the artificial root portion when healing and bone integration of the artificial root portion is complete, and a dental prosthetic appliance such as a crown, denture, partial denture or bridge is attached to the coronal portion. The prosthetic coronal portion must pass through the connective tissue and overlying mucosa for attachment to the root. The coronal portion can be screwed onto the artificial root. A problem with this type of attachment system is that the coronal section may loosed by unscrewing slightly.

An object of our invention is to provide an endosseous dental implant system which resists loosening between an artificial root and coronal portion.

Another object of our invention is to provide the endosseous dental implant with an apparatus between the artificial root and the coronal portion which resists torque.

It is a further object of our invention to provide such a system with an internal jam nut interposed between the root and the coronal portion, and enclosed within either the root or the coronal portion.

These and other objects of our invention will be apparent from the following description taken with reference to the accompanying drawings.

SUMMARY OF THE INVENTION

To achieve the foregoing objects, we have invented an endosseous dental implant system comprising an artificial root and a coronal portion. Interposed between the artificial root and the coronal portion is an internal jam nut. The jam nut is captured inside the root and permits the coronal portion to be locked to the artificial root.

DETAILED DESCRIPTION OF THE PREFERRED EMBODIMENT

We will now describe our preferred embodiment of our invention by reference to the accompanying drawings. Like numerals designate like parts in each of the figures.

Figure 1:
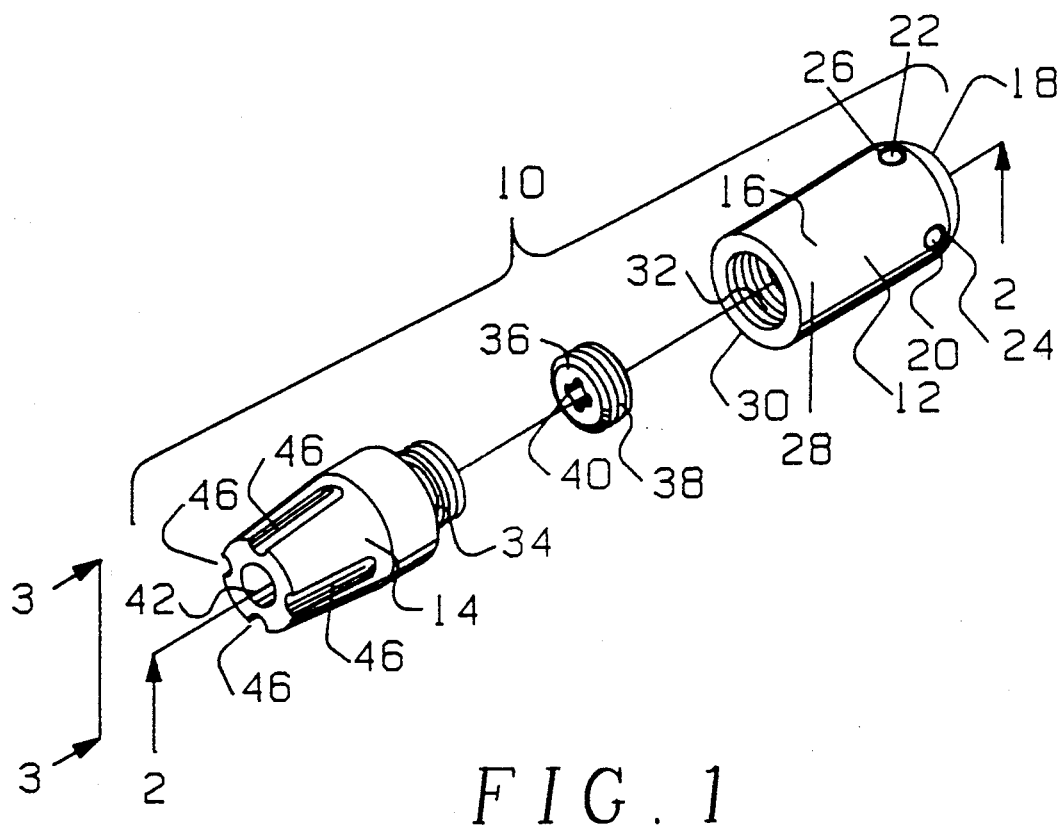
FIG. 1 is an exploded perspective view of an endosseous dental implant system according to our present invention.
Figure 2:
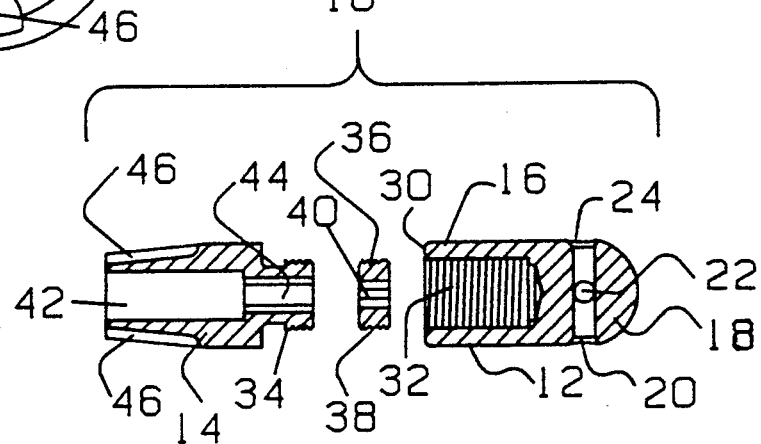
FIG. 2 is a through section of each of the components shown in FIG. 1 taken along line 2—2 of FIG. 1.

As shown in FIG. 1 an endosseous dental implant system 10, according to our present invention, comprises an artificial root member 12 which can implanted into the bony structure of a patient's jaw. The artificial root 12 supports a coronal portion or member 14. The artificial root 12 comprises a generally cylindrical shaft 16 with a rounded end 18. Two orthogonal through bores 20, 22 provide areas for bony ingrowth to aide the artificial root 12 to become securely attached to a patient's jaw. Edges of the bores 20, 22 are counter-sunk 24, 26. In our preferred embodiment, an outer surface 28 of the root 12 is coated with hydroxyapatite to promote the integration of the root with the bony structure of the jaw. As shown in FIG. 1 and FIG. 2, at a flat upper surface 30 of the artificial root 12, there is a threaded bore 32. The bore 32 is coaxial with the shaft 16.

We have found that when a root and coronal portion of a endosseous prosthesis are screwed together there is a tendency for the coronal portion to unscrew slightly, weakening the attachment between the two parts and misaligning, however slightly, and prosthetic structure attached to the coronal portion. To overcome this tendency, we have invented an internal jam nut 36. The jam nut comprises a suitable biocompatible substance, such as titanium, which has threads 38 along its external surface and which can be screwed into the threaded bore 32 in the root. In our preferred embodiment, we have used a spline bore 40, suitable for receiving an splined wrench, to drive the jam nut 36 into the threaded bore. Once the jam nut has been placed in threaded bore, the coronal portion 14 can be screwed into the root 12. To facilitate attachment of the coronal portion, a bore 42 provides access to a hexagonal through bore 44 in the coronal portion. We have also provided grooves 46 on the coronal portion so that an artificial tooth or other dental structure can be securely attached to the coronal portion.

Figure 3:
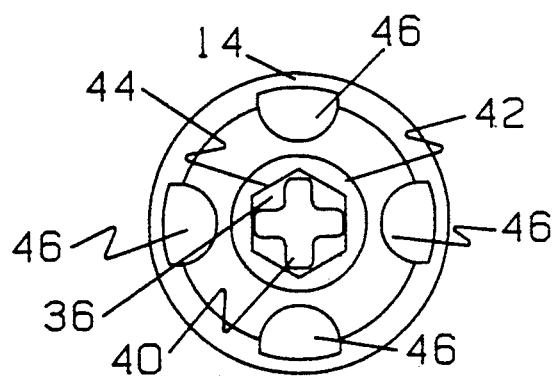
FIG. 3 is a top view of the implant system taken in the direction shown by line 3—3 of FIG. 1.

As can be seen in FIG. 3, the spline bore 40 can be turned through the bore 42 and the hexagonal through bore 44 in the coronal portion 14, even when the coronal portion is installed on the root 12. This permits the jam nut 36 to be tightened against the coronal portion 14 to establish a desired preload. In practice, we have found that a nominal 0.050 inch hexagonal bore can be used with a nominal 0.050 inch spline. This is because the hexagonal bore is nominally measured from flat to flat. The point to point measure is about 0.058 inch. Filleting and other standard features of a spline result in a effective diameter of about 0.048 inch, so the jam nut can be driven with the coronal portion installed.

The internal jam nut allows the coronal portion to be mounted on the root with an initial preload which acts to resist unscrewing. Because the jam nut is adjustable in the threaded bore, the effective height of the prosthesis 10 can be adjusted in situ after the root is permanently implanted. The orientation of the coronal portion can be changed without sacrificing a desired preload. In addition, the jam nut is completely enclosed within the prosthesis. In our illustrated embodiment, it is enclosed within the root 12.

The internal jam nut, when screwed against the bottom of the coronal portion, allows the coronal portion once seated on the root to resist unscrewing. The combination of the preload and friction between the coronal portion's surfaces gives the increased resistance to unscrewing.

Our invention may be embodied in other specific forms without departing from the spirit or essential characteristics thereof. The present embodiment is considered in all respect to be illustrative and not restrictive, the scope of our invention being indicated by the appended claims rather than the foregoing description and all changes which come within the meaning and range of equivalency the claims are therefore intended to be embraced therein.

We claim as our invention:

1. A prosthetic dental implant attachment system for mounting a prosthetic device in fixed relationship to a jaw of patient comprising:

a root member for securing the implant system to the jaw, said root member having an axial threaded bore opening at an exposed end of said root member;

a coronal member, said coronal member having a threaded shaft for engaging said axial threaded bore for mounting said coronal member on said root member in fixed relationship thereto and a central bore passing though said coronal member and said threaded shaft;

said threaded shaft having a bottom end distal from said coronal member; and a jam nut threadedly received within said threaded bore between said root member and said coronal member, said jam nut having a wrench engaging means accessible through said central bore;

whereby said jam nut can be tightened against said bottom end of said coronal member after said coronal member has been mounted on said root member.

2. The prosthetic dental implant attachment system according to claim 1 wherein the wrench engaging means comprises a splined bore.

3. The prosthetic dental implant system according to claim 2 wherein the central bore comprises a hexagonal through bore.

4. The prosthetic dental implant system according to claim 1 wherein the central bore comprises a hexagonal bore.

5. The prosthetic dental implant system according to claim 4 wherein the wrench engaging means comprises a spline bore.

* * * * *